United States Patent [19]
Bierke-Nelson et al.

[11] Patent Number: 5,856,102
[45] Date of Patent: Jan. 5, 1999

[54] HOME/SELF-STORAGE TO IMPROVE DNA BANKING

[76] Inventors: Diane Lynn Bierke-Nelson; Stuart James Nelson; Joshua James Nelson; Jesse Stuart Nelson, all of 106 N. 21st St. East, Superior, Wis. 54880-6546

[21] Appl. No.: 806,205

[22] Filed: Feb. 26, 1997

[51] Int. Cl.⁶ ............................. C12Q 1/68; B65B 11/48; B65D 69/00
[52] U.S. Cl. ............................. 435/6; 206/223; 206/233; 53/460; 435/810
[58] Field of Search ................................... 435/4, 6, 810; 935/77, 78; 206/233, 223, 803, 570, 438; 53/460

[56] References Cited

U.S. PATENT DOCUMENTS

| 5,101,970 | 4/1992 | Turner | 206/223 |
|---|---|---|---|
| 5,211,286 | 5/1993 | Turner | 206/223 |

OTHER PUBLICATIONS

Kirby, editor DNA Fingerprinting: An Introduction. W.H. Freeman & Co. New York (1992) pp. 51–74.

Thompson and Thompson Genetics in Medicine 5th Ed. 1991 W.B. Saunders Ch 3 pp. 36, 38; Ch. 4 pp. 90, 91; Ch 5 p. 97; Ch 5 p. 105, 106, 109, 110, 112, 113, Ch 6 pp. 115, 116, 119, 127, 138 (Complete Chapters Will Be Furnished Upon Request).

"DNA Dignosis of Leber's Hereditary Optic Neuropathy by Using Dried Blood Specimens" Yukihiko, Mashima, M.D., et. al. Am Jr. of Opthalmology Dec., 1993 pp. 773–774.

"PCR Analysis of Hair Root Specimens to Detect Tay–Sachs Disease Carriers in Ashkenazi Jews" Ruby Brillante, et. al. Clinical Chemistry vol. 41 No. 2, 1995 pp. 321–322.

"The Impact of Cancer Genetics on Oncology Nursing Practice" Paula Trahan Rieger Nursing Interventions in Oncology p. 17.

DNA Isolation by a Rapid Method from Human Blood Samples . . . Lahiri, DK Biochemical Genetics 31(78), 1993 Aug. Abstract.

"Detection of Very–Rare–Copy DNA in 0.2–ml Dried Human Blood Blots," Fishbein, WN et.al. Biochemical & Molecular Medicine 56(2) 1995 Dec. Abstract.

"Multiplex PCR Amplification from the CFTR Gene Using DNA Prepared from Buccal Brushes/Swabs" Richards, B. et. al. Human Molecular Genetics 2(2) 1993 Feb. Abstract.

"The Effect of Storage on Guthrie Cards: Implications for DNA Amplification" Makowskies et. al. Annals of Clinical & Laboratory Science 26(5) 1996 Sep.–Oct. Abstract.

"Finger Prick Blood Testing in Leber Hereditary Optic Neuropathy" Mackey D., et. al. British Jr. of Opthalmology 77(5) 1993 May Abstract.

*Primary Examiner*—W. Gary Jones
*Assistant Examiner*—Debra Shoemaker

[57] ABSTRACT

The invention is the improved process and method of DNA banking in which DNA or other genetic material is collected and stored, preserved, banked in a home/self-storage setting. Home/self-storage is to mean "not commercially banked." The invention includes the manufacture of kits designed to collect and bank DNA and other genetic material in a home/self-storage setting. The objective of the invention is to preserve genetic material in the event that it is needed for genetic analysis, genetic testing, genetic diagnosis, genetic therapy, forensic analysis, identification.

5 Claims, No Drawings

HOME/SELF-STORAGE TO IMPROVE DNA BANKING

BACKGROUND OF THE INVENTION

DNA banking is a term used when people have a body sample such as blood or cheek cells or body tissue stored in a large commercial place of business or a research laboratory or a university or college or health institute or the like. The bank or the lab may subject the sample to an initial process such as DNA extraction before storage. The bank or laboratory may use special environmental storage and preservation conditions such as freezing or transformed cell lines. In addition, commercial institutions which offer banking of DNA and other genetic material might decide to discontinue the offering of this service, go out of business, be the target of a business takeover, change its array of services provided. These events have happened, and it leaves the owner of the DNA/genetic samples with the possibility of their samples being lost, transferred to a new place of storage, etc. Also, commercial institutions which store genetic material are subject to changing federal and state statutes which make it difficult for them to offer DNA banking. For example, there is an initiative in the United States that DNA samples should be disposed of after genetic testing of these samples. This hinders the effort to store and bank these samples for future use. Also, there is initiative that DNA used for research purposes should be disposed of shortly after its use. In essence, these legislative issues are being driven by the idea of insuring that an individual's genetic make-up be confidential if so desired.

Many individuals, companies, institutions rely on the collection and banking of one sample of genetic material for possible future use. Our process encourages that human genetic samples from several different body sites are collected for banking. For the following reasons and to take into account the following genetic contingencies, the collection of genetic material from several different human body sites for possible future use in genetic analysis or genetic testing represents an improvement over the collection of samples from one body site. There are different types of genetic mutations: germ line and somatic cell. It is likely that a germ line mutation would probably be present in most if not all of the cells of an individual's body. In this case, one DNA gene sample would probably give a fairly accurate account when that DNA was analyzed and tested for the genetic aberrance. A germline mutation occurs or is present in the egg or sperm which together form the zygote at the beginning of development. This is why most if not all of the cells would carry the genetic alteration being sought. Imprinting and other phenomenon may present exceptions. However, the somatic cell mutation or genetic alteration may happen during or after development. In effect then only cells that originate or come from that cell would carry the mutation and the body would show mosaicism. It may be then that a sample taken from one body site might not have come from the line of cells produced from the mutated somatic cell. In that event, the genetic alteration being sought would be missed if only that sample was available for testing. It would be better to have more than one genetic DNA sample available for testing to take into account this contingency or possibility. Our process and method helps to guard against these genetic variations. It is important to understand that as the zygote divides and fetal embryonic development begins, three embryonic germ layers of cells form: ectoderm, mesoderm, endoderm. Each of these embryonic layers gives rise to various tissues and organs. The ectoderm gives rise to epidermis, hair, brain, spinal column, sweat glands, certain parts of the eye, inner ear, epithelium of the nose/mouth/anus. The mesoderm gives rise to dermis, muscle, cartilage, bone, blood, connective tissue, blood vessels, reproductive organs, kidneys. The endoderm gives rise to the linings of the digestive tract and the respiratory tract, urethra, urinary bladder, gallbladder, liver, pancreas, thyroid, parathyroid, thymus. Genetic mutations leading to increased risk for certain diseases could be somatic and reside only in one or two of these three embryonic germ layers. Current technology allows us to compose and manufacture a multiple sample DNA collection kit which collects samples from the mouth cheek cells which are derived from ectoderm, hair follicles which are derived from ectoderm and mesoderm, and blood which is derived from mesoderm. As new developments, technology, and findings come about, our process is designed to include or substitute in our Kit a sample of some type of cell(s)/tissue(s) which is/are derived from endoderm. One possibility is to collect and store some type of sample such as urethral discharge, urine, urine sediment, urine filtrate (urine passed through a filter and the filtered material collected and stored) which may contain endoderm and/or mesoderm. Another possibility is to collect and store some type of material from the lining of the digestive tract which is derived from endoderm. Feces could possibly be dried, filtered, centrifuiged, or processed in some type of fashion suitable for DNA collection and storage/preservation. Another possibility is the collection of some type of respiratory tract material or secretion which contains endodermal material.

These additional ideas for collection of DNA for banking do not have to be limited to endodermal tissue. New discoveries in the future may make it possible for using better ways to collect and store DNA samples of mesodermal and ectodermal tissue/cells. Sorting out the phenomenon and influences of incomplete penetrance, variable expressivity, genetic-environmental interactions, inherited susceptibility mutations, acquired susceptibility mutations, baseline chance, imprinting, mosaicism, gene products, and others, most likely will require multiple cell samples from individuals and families. Likewise, diseases influenced by genetic factors can be affected through different mechanisms. Sometimes a disease or risk for a disease is influenced by Mendelian inheritance whereby a gene on a chromosome is the deciding factor. (Still, even in this case the germline versus somatic issue argues for multiple sample collection). On the other hand, sometimes a disease or risk for a disease is influenced by mutations or alterations of different genes on different chromosomes. This is called multifactorial. In the multifactorial scenario, the case of germnine versus somatic also exists. Let's look at the following hypothetical but realistic example which argues for multiple DNA sample collection. Mutation A, present on Chromosome #4, and Mutation B, present on Chromosome #7, contribute to increased risk to Disease X. Both must be present for the increased risk to occur. Mutation A is germnine so that it would be detected from a blood or mouth cheek cell DNA sample collected and stored. However, Mutation B is somatic cell and occurs only in progeny cells produced from the somatic cell first affected. For the sake of argument, let's say that blood cells are not part of the lineage arising from the somatic cell first affected with the Mutation B but cheek cells are part of the lineage. When blood cells from this individual were to be analyzed, Mutation A would be detected but not Mutation B. The genetic interpretation would be in error, inconclusive, or incomplete since both Mutation A and Mutation B would have to be detected to say that a person had increased susceptibility or risk to develop Disease X. In this case cheek cells would yield a more accurate interpretation.

If DNA from various body sources is found to vary even slightly, it could make a difference in the accuracy and efficiency of DNA genetic testing and diagnostic applications. There is also the possibility that genetic testing could be done with or is more effective and accurate with components associated with DNA, e.g. histones, proteins, glycoproteins, other gene products, ribose nucleic acid (RNA), etc. (At present the terminology for genetic material revolves around the usage of the words deoxyribose nucleic acid (DNA) and gene. This terminology may come to include other components which could be used in genetic analysis or genetic testing or genetic diagnosis. We are implying the collection of genetic material in its broadest sense, although we sometimes use the current accepted terminology involving DNA and genes.) It is possible that DNA in association with these components or in conjunction with these components allows for more accurate and efficient genetic testing and diagnosis. It may be that these associated products may be found in one body source but not another.

BRIEF SUMMARY OF THE INVENTION

The invention is the improved process and method of DNA banking in which DNA or other genetic material is collected and stored, preserved, banked in a home/self-storage setting. Home/self-storage is to mean "not commercially banked." The invention includes the manufacture of kits designed to collect and bank DNA and other genetic material in a home/self-storage setting. The objective of the invention is to preserve genetic material in the event that it is needed for genetic analysis, genetic testing, genetic diagnosis, genetic therapy, forensic analysis, identification.

DETAILED DESCRIPTION

The invention is an improved process and improved method of DNA banking or banking of genetic material.
Detailed Description of the Home/Self-Storage Process and Method In our storage system there is no storage in a large commercial bank or lab, there is no processing of the initial sample other than simple drying and storage (in the future urine may need to be filtered or allowed to settle to obtain urine sediment for storage, in the future other body fluids may need to be filtered or allowed to settle to obtain sediment or cells for storage), storage is done in a secure place at home or in a safety deposit box, in envelopes, in a file cabinet, or the like. These items make our system of storage different, yet useful, new, and unique from what others are doing or have done. The usefulness and advantages of this home/self-storage represent improvements to what is currently being done regarding preservation of genetic material from humans. The improvements include but are not limited to issues such as storage without refrigeration/freezing or special requirements, shipping and mailing without refrigeration/freezing or special requirements, increased privacy, better control of confidentiality, personal ownership, better control of the use of genetic samples and who has access to them, increased ability to prevent invasion of genetic privacy by health and life insurance companies, prevention of unauthorized testing and research, less chance of sample loss or mix-up, immunity from turmoil when commercial banks and laboratories decide not to offer banking anymore, better control over paternity issues, immunity from state and federal statutes which might make it difficult for commercial banks and laboratories to offer banking, etc.

Other companies, organizations, and individuals are engaged in the activity of collecting and/or storing and/or banking DNA. Their process is different than ours since our process involves the storage of genetic material in a home/self-storage setting. We know of no other process, method, or kit which has the features of home/self-storage. Our process is an improvement over other existing processes in that no one to our knowledge has manufactured an article or kit or composed a process or method whereby a human genetic sample or human genetic samples is/are stored in a home/self-storage process.

We feel that storage of DNA and other human genetic material in a home/self-storage setting gives one adequate assurance that:

1. The DNA or genetic material collected is stored, preserved, banked in a place which gives its owner more control over the privacy of owner's genetic make-up
2. The storage process is more stable in that commercial places of banking are subject to business take-overs, changes in services offered, bankruptcies, state and federal statutes which make it difficult to bank genetic material
3. The storage process is less subject to sample mix-up and loss
4. The storage process does not require special environmental conditions
5. The storage process allows for more convenient shipping and mailing In our storage process and method, it can be appropriate to store one sample of genetic material collected from one body site. However, an improvement is to collect and store more than one sample from the same body site or samples from several different body sites or both. We feel that collection and storage of DNA from multiple human body tissues, sites, places, cells, organs, and sources gives one adequate assurance that:

1. the DNA or genetic material collected and stored will be adequate in sample size,
2. able to withstand prolonged periods of storage, and that back-up samples are available
3. there will be a good mix of DNA or genetic material from different body sources since it may be found that DNA or genetic material from one source of the body is not exactly equivalent to that from another source
4. the correct DNA or genetic material is collected and stored since it may be found that the DNA or genetic material from one source is not exactly equivalent to that from another source
5. there is a better chance that the DNA or genetic material will survive the storage process since several samples are available
6. the gamut of contingencies inherent in the field of genetics, (e.g. mosaicism, endodermal/ectodermal/mesodermal issues, gerrnline/somatic issues, multifactorial/Mendelian issues, etc.) are taken into account
7. RNA, proteins, and other associated components which might be needed for genetic analysis and testing are in the stored samples Detailed Description of the Kit We have manufactured a kit to carry out these improvements in DNA banking. The kit represents the current best mode of collecting samples of human genetic material.

Storage of these multiple samples is in a home/self-storage setting. We are supplying items which allow individuals to store collected DNA genes at home, in a file cabinet, in a safety deposit box, in envelopes, etc. in home-type of storage (self-storage). Our process is unique and represents a new process. The kit is designed for the collection of DNA genes from multiple body sites with subsequent storage of these multiple samples in a home/self-storage setting. The kit can be used to collect just one sample from one body site or several samples from the same body site.

At present the collection process and home/self-storage process can be described as follows. A small brush approximately 6 inches in total length with a handle approximately 5 inches in length and a set of bristles approximately 1 inch in length is used to collect mouth cheek cells and scrapings. Following collection using specified instructions, the brush is placed into a container approximately 6 inches in length with a diameter of approximately ⅝ inch. This container is labeled according to instructions and is placed in a 6 ½ inch by 3 ½ inch envelope which is labeled for contents and storage.

Hair from the human head is collected using an ordinary comb. Loose hair which accumulates in the comb is taken and after cutting off and discarding the ends not containing the hair follicles, the remaining hair strands containing the hair follicles are placed in a 6 ½ inch by 3 ½ inch envelope which is labeled for contents and storage. When an individual is to have blood drawn by a licensed health care provider, the individual requests that drops of blood be applied to specialized cards of paper approximately 4 inches by 3 inches. The blood drops are allowed to dry and then this card is placed in an envelope 6 ½ inches by 3 ½ inches which is labeled for contents and storage. All of these envelopes are stored in a secure place in a home/self-storage setting such as a file drawer, safety deposit box, file cabinet, file drawer, etc. The DNA is not extracted at the time of storage but can be extracted latter when and if a sample is to be tested and genetically analyzed.

The components of the a kit designed to carry out these processes would possibly include:

Comb and/or any other device designed to collect hair and hair follicles containing DNA genes Specially-labeled storage envelope to store hair and hair follicles containing DNA genes Brushes and/or swabs and/or any other device designed to collect mouth cheek cells containing DNA genes Specially-labeled storage envelope and containers to store brushes/swabs/devices containing DNA genes Paper/cardboard/special paper or material to which blood can be applied and dried (may be specially-labeled)

Specially-labeled storage envelope and containers to store dried blood containing DNA genes Instruction sheets on how to collect and store DNA genes Beneficiary Designation Forms Family Notice Forms Brochures Information and educational articles Information Sheets Questionnaire Family Medical History Forms These items listed directly above constitute what we consider the "best mnode" for collection of samples of genetic material and the "best mode" of home/self storage of a sample or samples of genetic material.

It may be that hair follicles from other parts of the body constitute the best mode in the future. It may be that cells from other parts of the body can be collected via a brush or swab in the future and that this process represents the best mode in the future. It is possible that DNA may be collected and effectively stored from skin scrapings, nasal wash or scrapings or secretions, eye secretions, mucous membranes, saliva, expectorant, toenails, fingernails, sputum, urine, urine sediment, genital secretions, sperm, semen, vaginal and cervical secretions, feces, fecal matter or other body sites.

Consequently, the kit and the items in the kit may be somewhat altered in the future in order to accommodate the best mode and the latest technology.

We claim:

1. A method for collecting and storing DNA and other human genetic material in a home/self-storage setting so that the DNA and other human genetic material is available for future use, the method comprising:

(a) collecting samples of blood, mouth cheek cells, and head hair follicles; and (b) storing the samples without refrigeration or freezing in labeled envelopes in a secure place in a home/self-storage system.

2. The method of claim 1 wherein the step of collecting blood further comprises:

(a) following collection of blood from an individual by a licensed health care professional, placing drops of blood on a filter paper card labeled for identification;

(b) drying the blood; and (c) placing the card in a labeled envelope.

3. The method of claim 1, wherein the step of collecting mouth cheek cells further comprises:

(a) brushing the inside of the mouth cheek with a brush;

(b) drying the brush; and (c) placing the brush in a container and placing the container in a labeled envelope.

4. The method of claim 1, wherein the step of collecting head hair follicles further comprises:

(a) collecting loose head hair which accumulates in a comb;

(b) cutting off and discarding the end of the hair not containing hair follicles; and (c) placing the hair strands containing hair follicles in a labeled envelope.

5. The method of claim 1, wherein the secure place in a home/self storage setting is selected from the group consisting of a file cabinet, file drawer, lock box and safety deposit box.

* * * * *